US006613812B2

(12) United States Patent
Bui et al.

(10) Patent No.: US 6,613,812 B2
(45) Date of Patent: Sep. 2, 2003

(54) DENTAL MATERIAL INCLUDING FATTY ACID, DIMER THEREOF, OR TRIMER THEREOF

(75) Inventors: Hoa T. Bui, Mendota Heights, MN (US); Brant U. Kolb, Afton, MN (US); Sumita B. Mitra, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/753,945

(22) Filed: Jan. 3, 2001

(65) Prior Publication Data

US 2002/0129736 A1 Sep. 19, 2002

(51) Int. Cl.$^7$ .......................... A61K 6/083; C08K 9/06; A61C 5/00
(52) U.S. Cl. ....................... 523/116; 523/115; 523/118; 523/120; 523/212; 523/217; 433/226; 433/228.1
(58) Field of Search .................. 523/115, 116, 523/118, 120, 212, 217; 433/226, 228.1

(56) References Cited

U.S. PATENT DOCUMENTS

| | | | |
|---|---|---|---|
| 3,066,112 A | 11/1962 | Bowen | 260/41 |
| 3,539,533 A | 11/1970 | Lee, II et al. | 260/47 |
| 3,629,187 A | 12/1971 | Waller | 260/41 R |
| 3,655,605 A | 4/1972 | Smith | 260/29.6 M |
| 3,709,866 A | 1/1973 | Waller | 260/27 R |
| 3,751,399 A | 8/1973 | Lee, Jr. et al. | 260/47 UA |
| 3,766,132 A | 10/1973 | Lee, Jr. et al. | 260/41 A |
| 3,814,717 A | 6/1974 | Wilson et al. | 260/29.6 M |
| 3,860,556 A | 1/1975 | Taylor | 260/42.52 |
| 4,002,669 A | 1/1977 | Gross et al. | 260/486 B |
| 4,043,327 A | 8/1977 | Potter et al. | 128/89 R |
| 4,071,424 A | 1/1978 | Dart et al. | 204/159.15 |
| 4,115,346 A | 9/1978 | Gross et al. | 260/42.15 |
| 4,143,018 A | 3/1979 | Crisp et al. | 260/29.6 M |
| 4,209,434 A | 6/1980 | Wilson et al. | 260/29.6 H |
| 4,259,117 A | 3/1981 | Yamauchi et al. | 106/35 |
| 4,292,029 A | 9/1981 | Craig et al. | 433/228 |
| 4,308,190 A | 12/1981 | Walkowiak et al. | 260/29.7 |
| 4,327,014 A | 4/1982 | Kawahara et al. | 523/116 |
| 4,379,695 A | 4/1983 | Orlowski et al. | 433/217 |
| 4,387,240 A | 6/1983 | Berg | 556/440 |
| 4,404,150 A | 9/1983 | Tsunekawa et al. | 260/927 R |
| 4,642,126 A | 2/1987 | Zador et al. | 51/295 |
| 4,652,274 A | 3/1987 | Boettcher et al. | 51/298 |
| 4,737,593 A | 4/1988 | Ellrich et al. | 568/15 |
| 4,772,530 A | 9/1988 | Gottschalk et al. | 430/138 |
| 4,872,936 A | 10/1989 | Engelbrecht | 156/307.3 |
| 4,874,450 A | 10/1989 | Gottschalk | 156/275.5 |
| 4,954,414 A | 9/1990 | Adair et al. | 430/138 |
| 5,055,372 A | 10/1991 | Shanklin et al. | 430/138 |
| 5,057,393 A | 10/1991 | Shanklin et al. | 430/138 |
| 5,063,257 A | * 11/1991 | Akahane et al. | 523/116 |
| 5,154,613 A | * 10/1992 | Cohen | 433/228.1 |
| 5,154,762 A | * 10/1992 | Mitra et al. | 106/35 |
| 5,332,429 A | 7/1994 | Mitra et al. | 106/35 |
| 5,453,456 A | 9/1995 | Mitra et al. | 523/116 |
| 5,545,676 A | 8/1996 | Palazzotto et al. | 522/15 |
| 5,883,153 A | 3/1999 | Roberts et al. | 523/116 |
| 6,238,212 B1 | * 5/2001 | Khachatoorian et al. | 433/89 |

FOREIGN PATENT DOCUMENTS

| | | |
|---|---|---|
| EP | 173567 | 3/1986 |
| EP | 323120 | 7/1989 |
| GB | 2108132 | 5/1983 |
| GB | 2310855 | 9/1997 |
| WO | WO 00/55253 | 9/2000 |

OTHER PUBLICATIONS

"Grant & Hackh's Chemical Dictionary," Grant and Grant, eds., 5$^{th}$ Edition, McGraw–Hill Inc., New York, Title page, Publication page and pp. 22, 24, 230 and 290 (1987).

* cited by examiner

*Primary Examiner*—Tae H. Yoon
(74) *Attorney, Agent, or Firm*—Doreen S. L. Gwin

(57) ABSTRACT

A dental composition is provided comprising
(a) a part A comprising fluoroaluminosilicate glass that has been surface treated with agents selected from the group consisting of silane, silanol and combinations thereof, and at least one fatty acid, dimer thereof, or trimer thereof; and
(b) a part B comprising at least one polyacid. The composition further comprises resin that can be curable or non-curable and at least one initiator. The composition exhibits adhesion to dentin, and the treated FAS glass contained therein does not settle out with time.

19 Claims, No Drawings

DENTAL MATERIAL INCLUDING FATTY ACID, DIMER THEREOF, OR TRIMER THEREOF

TECHNICAL FIELD

The present invention provides a dental composition with high loading of reactive glass. In particular, the composition contains, among other components, treated reactive glass, such as fluoroaluminosilicate glass, and a fatty acid additive. Even with a high loading of reactive glass, the composition is stable during storage, does not phase separate, and has good physical properties making it suitable in various dental applications.

BACKGROUND

Fluoroalumuniosilicate (FAS) glass has been used widely in dental compositions. They are known fluoride releasing materials. The glass can be treated with surface treating agents such as silanes. Some skilled in the art have used treated fluoroaluminosilicate glass in dental cements and liners, among other applications.

U.S. Pat. No. 5,883,153 (Roberts et al.) discloses a dental composition comprising a resin composition made of (a) radical polymerizable compound, (b) a curing agent, and (c) fluoride-ion sustained release preformed glass ionomer filler. The glass ionomer filler may be surface treated with agents such as silane compounds.

Some skilled in the art have used fatty acids in dental compositions for various reasons. For example, U.S. Pat. No. 5,154,613 (Cohen) discloses a dental cement for a temporary dental prosthesis. The cement is in the form of a paste. The paste consists of metal a oxide and a metal hydroxide. Preferably, the metal oxide is the oxide of zinc, calcium, mercury, copper, silver, and barium. The paste may also include a fatty acid in an amount between 0.1 and 25 weight percent, preferably those chosen from $C_8$ to $C_{18}$ saturated acids. It is stated that the fatty acids function to (1) increase the adhesion of the cement by etching the temporary prosthesis, and (2) reduce the adhesion of the cement to dentin.

UK Patent Application No. 2 108 132 discloses a dental cement containing first and second components. The first component is a powder of fine particles of zinc oxide, calcium hydroxide, magnesium oxide or magnesium hydroxide. None of the particles is a reactive glass. The particles of the first component are surface treated with a fatty acid such as stearic or oleic acid. The second component is an organic liquid, such as eugenol. It is stated that providing a fatty acid surface coating on the particles facilitates and speeds up mixing and allows a higher proportion of the metal oxide or hydroxide to be incorporated into a dental cement of a given consistency.

While the foregoing technology may be useful, other dental compositions are sought.

SUMMARY

The present invention provides, for the first time, a dental composition having, among other components, treated acid-reactive filler and a fatty acid as an additive. The inventive material has a viscosity at which it can be easily dispensed from a device, such as a syringe, without being stringy.

In brief summary, the dental composition comprises (a) a part A comprising fluoroaluminosilicate glass that has been surface treated with agents selected from the group of silane and silanol, and at least one fatty acid; and (b) a part B comprising at least one polyacid. The composition further comprising at least one resin and at least one initiator, the resin and initiator residing in either part A or part B. Kits and methods of using the dental composition are also disclosed.

One illustrative method comprises the acts of (a) providing a dual barrel syringe of a dental composition recited in the immediate paragraph above stored in the barrels such that part A resides in a first barrel and part B resides in a second barrel; (b) dispensing an amount of the dental composition onto a mixing pad; (c) mixing parts A and parts B together to form the dental composition; (d) supplying a sufficient amount of water; and (e) applying the dental composition to a patient's dental structures.

One advantage of the present invention is that the composition can be formulated and packaged such that parts A and B are both pastes or one being a paste (typically part A) and the other a liquid (typically part B). The paste-paste or paste-liquid combination allows for easy mixing of the two parts prior to use. Previously, some dental compositions have typically been supplied in powder-liquid form. For example, the dental cement in UK Patent Application No. 2 108 132 uses a zinc oxide powder. The powder presents drawbacks during the mixing process because more skill and care is required to dispense adequate amounts of the powder and liquid in making the dental composition.

Another advantage of the present invention is that the acid-reactive filler, in particular, the fluoroaluminosilicate (FAS) glass, is treated with a silane or silanol solution. Such treatment allows for increase FAS glass loading in the inventive composition and provides for increase in working time, both being desirable attributes in a dental composition. As an additional benefit, the high loading of the reactive glass fillers yield a radiopaque dental composition.

Yet another advantage is that the inventive composition is stable and does not settle during storage. The fillers can settle out of a dental composition during storage. Because of the size and density of the treated FAS glass filler, maintaining a homogeneous system can present a challenge. It is believed that the use of fatty acids minimizes, if not nearly eliminate, the filler from settling. The fatty acid imparts a yield stress to the dental composition thereby keeping the reactive glass particles from settling.

Yet with such a high loading of reactive glass, the physical and rheology properties of the inventive material remain well suited for dental applications. In particular, the inventive composition has good adhesion to dental structures and good compressive strength.

The inventive dental composition can be used in various applications. Such applications include dental adhesives, artificial crowns, anterior or posterior fillings, casting materials, cavity liners, cements, coating compositions, mill blanks, adhesives and cements for affixing orthodontic brackets and appliances, endodontic cements, restoratives, prostheses, and sealants. The materials can be placed in the mouth and cured in situ. Alternatively, it may be fabricated into a prosthesis outside the mouth and subsequently adhered in place in the mouth.

DETAILED DESCRIPTION OF THE INVENTION

The inventive composition can be visually described as similar to whip cream (such as Cool Whip®, from Kraft Foods), shaving cream or hair mousse dispensed from a pump. The composition has adhesion to dentin greater than about 5 MPa when tested according to the Adhesive Test Method, as described below in the Examples. The treated FAS glass has the ability to release useful amounts of fluoride ion when made into a cured dental composition. Fluoride release can be measured using the procedure set out in Example 18 of EP 0 323 120 B1. The composition has a compressive strength greater than about 10,000 psi when tested according to Compressive Strength Test Method, as described below in the Examples.

As stated, in one embodiment, the inventive composition is supplied as a two-part system, a part A and a part B. The viscosity of part A is typically greater than about 50,000 cps, preferably between 150,000 to 300,000 cps when measured at or near room temperature (about 25° C.) using a Brookfield viscometer using a T-D spindle with a conversion factor equal to 32,000. Typically, a dental practitioner mixes the two parts immediately prior to use. As the two parts are mixed, the acid-base FAS curing reaction begins. Subsequent curing of the ethylenically-unsaturated groups or the curable resin is done by curing agents and/or by light. Each component used to formulate parts A and B are discussed in detail below. Certain components such as the curable resin and the initiator may reside in either part A or part B, as further explained below.

Acid-Reactive Filler

Part A comprises about 5% to 90%, preferably about 40% to 80% by weight acid reactive filler, based on the total weight of the components in part A. Suitable acid-reactive fillers include metal oxides, metal salts, and glasses. Of these, glasses are preferred. Suitable metal oxides and metal salts are disclosed in U.S. Pat. No. 5,154,762 at column 3, lines 55 to 62. Suitable glasses include borate glasses, phosphate glasses, and fluoroaluminosilicate (FAS) glasses, which is particularly preferred. The FAS glasses are described in U.S. Pat. Nos. 3,655,605; 3,814,717; 4,043,327; 4,143,018; 4,209,434; and 5,063,257. The glass contains leachable fluoride to provide useful protection against dental caries. The glass is sufficiently finely divided to provide easy mixing, rapid cure, and good handling properties. Any convenient pulverizing or comminuting methods can be used to make finely divided glasses. Ball-milling is one exemplary approach.

Preferably, the FAS glass particles are silanol treated according to U.S. Pat. No. 5,332,429 (Mitra et al.). In brief summary, the finely divided FAS glass particles described above can be treated by mixing them with an aqueous silanol treating solution. The solution contains (1) monomeric, oligomeric, or polymeric silanol, (2) water, and optionally (3) a volatile solvent. Once treated, the FAS glass particles can be dried using any convenient technique. Oven drying in a forced air oven is recommended, with overnight drying temperatures of about 30° to 100° C. being preferred. The treated and dried FAS glass particles can then be screened or lightly comminuted to break up agglomerates. The resulting FAS glass particles can be incorporated into a dental composition by combining such particles in the presence of water with a resin.

According to U.S. Pat. No. 5,332,429, the silanol treatment solution is adjusted with an acid or a base to yield a non-neutral solution (or at least one silane that is not only ethylenically-unsaturated but acid- or base-functionalized is used). The treatment is done in the presence of water. Accordingly, the silane(s) is converted to silanol(s). The acid or base and the silanol react with the FAS glass. See column 2, lines 5 to 13. The resulting, treated FAS glass is an acid-reactive organofluoroaluminosilicate particulate glass having an ion-containing, siloxy-containing coating. The coating is made from a composition containing compounds of the formula $R_nSi(OH)_{4-n}$, wherein R is a non-hydrolyzable polymerizable organic group and n is one to three. The silanol treating solution contains silanes that can be ionic, nonionic or a combination thereof, and they can be monomeric, oligomeric or polymeric. Acidic or basic silanol treating solutions can be made using ionic or nonionic silanes. Various ionic and nonionic silanes are disclosed in U.S. Pat. No. 5,453,456 starting at column 3. A preferred silanol treating solution is an acidic aqueous silanol treating solution containing a monomeric, oligomeric or polymeric ethylenically-unsaturated silanol. Such a solution can be made by dissolving a monomeric, oligomeric, or polymeric ethylenically-unsaturated alkoxysilane in a volatile solvent and water. Various alkoxysilanes are disclosed in columns 3 and 4 of U.S. Pat. No. 5,453,456. The preferred silanol treating solution may optionally contain an additional organic compound or mixture of compounds. This additional organic compound independently has at least one polymerizable, ethylenically-unsaturated double bond and average molecular weight of all species used to treat the FAS glass of up to about 5000 units per double bond. The molecular weight of each species is determined against a polystyrene standard using gel permeation chromatography. Various additional organic compounds are described in columns 4 to 6 of U.S. Pat. No. 5,453,456. The water used in the silanol treating solution facilitates hydrolysis of the silane(s). To discourage premature solution condensation of the silanol, the water is preferably substantially free of fluoride and other contaminants. Deionized water is preferred. The water is present at about 20% to 99.9%, preferably about 30% to 95%, based on the total weight of the silanol treating solution. Also, the acid or base in the treating solution should present in an amount so as to promote hydrolysis of the silane to the silanol. The desired amount of acid or base can be monitored by measuring the pH of the treating solution. The acidic pH is 5 or less, preferably about 1 to 4.5. The basic pH is 8 or higher, preferably about 9 to 12. Various acids and bases are listed in column 6 of U.S. Pat. No. 5,453,456. The optional volatile solvent in the silanol treating solution functions to dissolve the silane(s) and to aid in the formation of a thin film of the silanol treating solution on the finely divided FAS glass particles. Various solvents are described in column 6 of U.S. Pat. No. 5,453,456. When used, the amount of solvent should be at least sufficient to dissolve the silane and form a homogenous single-phase solution. Typically the solvent is present at 40% or more, preferably 40% to 60% of the total weight silanol treating solution.

In one embodiment, the FAS glass is treated with a combination of silane treating agents—gamma-methacryloxypropyltrimethoxysilane and gamma-(polyalkylene oxide) propyltrimethoxysilane. These two agents are available commercially under product designation SILQUEST A-174 and SILQUEST A-1230, respectively, from OSI Specialties, Inc., Danbury, Conn.

Fatty Acid

In the present invention, the fatty acid component is used as an additive in part A. In other words, the fatty acid is not pre-coated on the acid-reactive fillers. The phrase "fatty acid," as used herein means an organic compound composed of an alkyl or alkenyl group containing 4 to 22 carbon atoms and characterized by a terminal carboxylic acid group. Dimers and trimers of the fatty acid (i.e., composed of alkyl or alkenyl groups containing 4 to 22 carbon atoms per carboxylic acid group) can also be used in the present invention. The fatty acid can be saturated or unsaturated. The inventive composition contains about 0.01% to 5%, preferably 0.1% to 1% fatty acid, dimer thereof, or trimer thereof, based on the total weight of the A components.

Useful fatty acids include the fatty acids of caprylic acid ($CH_3(CH_2)_6CO_2H$), capric acid ($CH_3(CH_2)_8CO_2H$), octadecanoic acid ($CH_3(CH_2)_{16}COOH$), commonly referred to as stearic acid, and 9-octadecenoic acid ($CH_3(CH_2)_7CH{:}CH(CH_2)_7COOH$), commonly referred to as oleic acid. Particularly useful fatty acids are oleic acid and its dimer and trimer.

Resin

The resins used in this invention can reside in part A and/or in part B. The resins have sufficient strength, hydrolytic stability, and non-toxicity to render them suitable for use in the oral environment. Useful resins are (1) non-curable resins, and (2) curable resins, which are typically thermosetting resins. The non-curable resin can be a wide variety of resin, as long as it does not contain an acidic group. Typically, the non-curable resins are used as adjuvants and viscosity modifiers, as further described herein.

As used herein, the term "curable" describes the resin's ability to change its physical properties by polymerization. A purely illustrative change in the resin's physical property is a change from a less viscous state to a more viscous state through a polymerization reaction. This change is usually accomplished by the reaction of the resin initiated with an energy source, such as heat or light, and a catalyst or an initiator. Specifically, the curable resin contains at least one ethylenically-unsaturated moiety.

Preferably, the curable resin is made from one or more matrix-forming oligomer, monomer, or polymer, or blends thereof. Examples of useful resins include acrylate, methacrylate, urethane, carbamoylisocyanurate, epoxy resins, vinyl resins, and mixtures and derivatives thereof. U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150 disclose useful resins.

A useful class of curable resins contains free radically active functional groups and include monomers, oligomers, and polymers having one or more ethylenically unsaturated groups. Another useful class of curable resins contains cationically active functional groups. Yet another useful class of curable resins contains both cationically curable and free radically curable resins.

In the class having free radically active functional groups, suitable curable resins contain at least one ethylenically unsaturated bond, and are capable of undergoing addition polymerization. The term "(meth)acrylate" is used to mean acrylate and methacrylate. The free radically polymerizable materials include mono-, di- or poly-(meth)acrylates such as methyl (meth)acrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol triacrylate, pentaerythritol tetra(meth)acrylate, sorbitol hexacrylate, the diglycidyl methacrylate of bis-phenol A ("bis-GMA"), bis[1-(2-acryloxy)]-p-ethoxyphenyldimethyl bis[1-(3-acryloxy-2-hydroxy)]-p-propoxyphenyldimethylmethane, and trishydroxyethyl-isocyanurate trimethacrylate; the bis-(meth)acrylates of polyethylene glycols of molecular weight 200 to 500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

An alternative class of curable resins useful in the inventive material includes cationically active functional groups. Materials having cationically active functional groups include cationically polymerizable epoxy resins, vinyl ethers, oxetanes, spiro-orthocarbonates, spiro-orthoesters, and the like.

Initiators

For the curable resin systems described above, various initiators can be used. The initiators reside in either part A or part B.

For free radical polymerization, an initiation system can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically are capable of generating free radicals for addition polymerization upon exposure to light energy having a wavelength between 200 and 800 nm.

A variety of visible or near-IR photoinitiator systems may be used for photopolymerization of free-radically polymerizable resin. For example, a photoinitiation system can be selected from systems which initiate polymerization via a two component system using amine and α-diketone, as described in U.S. Pat. No. 4,071,424. Alternatively, the resin can be combined with a three component photoinitiator system such as described in U.S. Pat. No. 5,545,676 (Palazzotto et al.). The three component system includes an iodonium salt (i.e., a diaryliodonium salt), a sensitizer, and a donor. Each photoinitiator component is discussed in U.S. Pat. No. 5,545,676, column 2, line 27, to column 4, line 45.

Other useful free-radical initiators include the class of acylphosphine oxides, as described in EP Application No. 173567, U.S. Pat. No. 4,737,593 and UK Patent No. GB 2,310,855. Such acylphosphine oxides are of the general formula:

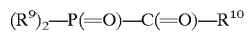

$$(R^9)_2{-}P({=}O){-}C({=}O){-}R^{10}$$

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O—, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be used in catalytically-effective amounts, such as from 0.1 to 5 weight percent, based on the weight of ethylenically-unsaturated compound present, of the acylphosphine oxide plus from 0.1 to 5 weight percent, based on the weight of ethylenically-unsaturated compound present, of the tertiary amine.

Commercially-available phosphine oxide photoinitiators capable of free-radical initiation when irradiated at wavelengths of greater than 400 to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis($\eta^5$-2,4-cyclopentadien-1-yl)-bis (2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye—counterion complex initiators comprising a borate anion and a complementary cationic dye. Borate salt photoinitiators are described, for example, in U.S. Pat. Nos. 4,772,530, 4,954,414, 4,874,450, 5,055,372, and 5,057,393. Borate anions useful in these photoinitiators generally can be of the formula $$R^1R^2R^3R^4B^-$$

wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium. Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups in the curable resin includes chemical initiator systems such as a combination of peroxide and amine. These initiators, which rely upon a thermal redox reaction using oxidizing and reducing agents, are often referred to as "auto-cure catalysts." The oxidizing and reducing agents are sufficiently water-soluble and have sufficient reduction and oxidation potentials to be effective free-radical generators. The term "sufficiently water-soluble" means that the agents readily dissolve in (and discourage separation from) the other components of the composition. They should react with or otherwise cooperate with one another to produce free-radicals capable of initiating polymerization of the ethylenically-unsaturated components. The reducing and oxidizing agents preferably are sufficiently shelf-stable and free of discoloration to permit their storage and use under typical dental conditions. The agents should be present in an amount sufficient to permit an adequate free-radical reaction rate. This rate can be evaluated by combining all of the ingredients of the composition except for the filler under safe light conditions and observing whether or not a cured mass is obtained.

Preferred reducing agents include, but are not limited to, amines, ascorbic acid, cobalt$^{II}$, chloride, ferrous chloride, ferrous sulfate, hydrazine, hydroxylamine (depending upon the choice of oxidizing agent) oxalic acid, thiourea, salts of a dithionite or sulfite anion, and salts of arylsulfinic acids. Preferred oxidizing agents include peroxides (e.g. benzoyl peroxide), salts of the transition metals in their higher oxidation states (e.g. Co$^{III}$, Fe$^{III}$, and Ce$^{IV}$), tert-butyl hydroperoxide, ferric chloride, hydroxylamine (depending upon the choice of reducing agent), perboric acid and its salts, and salts of a permanganate or persulfate anion. Hydrogen peroxide can also be used, although it has been found to interfere with the photoinitiator in some instances.

The amount of reducing agent and oxidizing agent should be sufficient to provide the desired degree of polymerization of the ethylenically-unsaturated component. The preferred amount for each of the reducing agent and oxidizing agent is about 0.01% to about 10%, more preferably about 0.02% to about 5%, based on the total weight (including water) of the uncured composition.

If desired, the reducing or oxidizing agent can be microencapsulated, which generally enhances shelf stability and permit packaging the agents together. For example, through appropriate selection of the encapsulant, both agents can be combined with the filler and kept in a storage-stable state. Likewise, through appropriate selection of a water-insoluble encapsulant, both agents can be combined with water and the polyacid and maintained in a storage-stable state.

Either water-soluble or water-insoluble encapsulants can be used. Water-insoluble encapsulants are preferred, as they generally provide better long term storage stability under moist or humid conditions. Although the use of a water-insoluble encapsulant may seem inappropriate when the inventive composition is water-based, it has been found that vigorous mechanical mixing generally will be sufficient to break apart the capsule walls and permit adequate release of the encapsulated reducing or oxidizing agent and subsequent cure of the composition.

Preferably the encapsulant is a medically acceptable polymer and a good film former. Also, the glass transition temperature ($T_g$) of the encapsulant preferably is above room temperature.

A wide variety of encapsulants can be used. Cellulosic materials such as cellulose acetate, cellulose acetate butyrate, ethyl cellulose, hydroxymethyl cellulose, and hydroxyethyl cellulose are preferred. Other encapsulants include polystyrene, polymethylmethacrylate, copolymers of polystyrene with other vinylic monomers, copolymers of methylmethacrylate with other ethylenically-unsaturated monomers, and other materials that are familiar to those skilled in the art of encapsulation.

The capsules themselves need not be perfectly spherical or uniformly shaped. They merely need to entrain or entrap the reducing or oxidizing agent in a manner sufficient to permit their storage without leading to undesirable premature polymerization.

To encapsulate the reducing or oxidizing agent in a water-insoluble encapsulant, it is preferred to dissolve the encapsulant in a suitable water-immiscible solvent such as methyl acetate, ethyl acetate or methylene chloride. Meanwhile, the reducing or oxidizing agent is dissolved in water. The water solution can then be added to the encapsulant and water-immiscible solvent solution. Preferably, stirring or other high-speed shear technique is used to promote microcapsule formation. The capsule shells are formed around the aqueous solution droplets either by evaporation of the water-immiscible solvent or by the addition of a second water-immiscible solvent (e.g., n-hexane) that will precipitate the encapsulant. The capsules can be removed by cooling and filtration.

To encapsulate the reducing or oxidizing agent in a water-soluble encapsulant, the dry reducing or oxidizing agent is preferably suspended in a stirred solution of the encapsulant in a water-immiscible organic solvent. Vigorous stirring can promote uniform encapsulation of the reducing agent or oxidizing agent. The capsules can be formed by evaporation or by precipitation and then removed using cooling and filtration.

In a further alternative, heat may be used to initiate the polymerization of free radically active groups. Suitable heat sources include inductive, convective, and radiant heat. Thermal sources should be capable of generating temperatures of at least 40° to about 150° C. under normal conditions or at elevated pressure. This procedure is preferred for initiating polymerization of materials occurring outside of the oral environment.

Yet another alternative class of initiators capable of initiating polymerization of free radically active functional groups in the curable resin are those that include free radical-generating thermal initiators. Examples include persulfates, potassium sulfates, and peroxides such as, e.g., benzoyl peroxide and lauryl peroxide, and azo compounds such as, for example, 2,2-azobis-isobutyronitrile (AIBN).

Part B contains at least one polyacid, which may be a curable resin or a non-curable resin. The polyacid need not be entirely water soluble, but it should be at least sufficiently water-miscible so that it does not undergo substantial sedimentation when combined with other components of Part B. Suitable polyacids are listed in U.S. Pat. No. 4,209,434, column 2, line 62, to column 3, line 6. The polyacid should have a molecular weight sufficient to provide good storage, handling, and mixing properties. A preferred $M_w$ is about 5,000 to 100,000, evaluated against a polystyrene standard using gel permeation chromatography.

In one embodiment, the polyacid is a curable resin. That is, it contains at least one ethylenically unsaturated group. Suitable ethylenically unsaturated polyacids are described in U.S. Pat. No. 4,872,936, e.g., at columns 3 and 4, and EP 323 120 B1, e.g., at about page 3, line 55, to page 5, line 8. Preferably, the numbers of acidic groups and ethylenically unsaturated groups are adjusted to provide an appropriate balance of properties in the dental composition. Polyacids in which about 10% to 30% of the acidic groups have been replaced with ethylenically unsaturated groups are preferred.

In other embodiments, the polyacid is non-curable resin. That is, it is an oligomer or polymer of an unsaturated acid. Preferably, the unsaturated acid is an oxyacid (i.e., an oxygen containing acid) of carbon, sulfur, phosphorous, or boron. More preferably, it is an oxyacid of carbon. Useful non-curable polyacids include polyalkenoic acids such as homopolymers and copolymers of unsaturated mono-, di-, or tricarboxylic acids. Preferred polyalkenoic acids can be prepared by the homopolymerization and copolymerization of unsaturated aliphatic carboxylic acids, e.g., acrylic acid, 2-choloracrylic acid, 3-choloracrylic acid, 2-bromoacrylic acid, 3-bromoacrylic acid, methacrylic acid, itaconic acid, maleic acid, glutaconic acid, aconitic acid, citraconic acid, mesaconic acid, fumaric acid, and tiglic acid. Suitable monomers that can be copolymerized with the unsaturated aliphatic carboxylic acids include unsaturated aliphatic compounds such as acrylamide, acrylonitrile, vinyl chloride, allyl chloride, vinyl acetate, and 2-hydroxyethyl methacrylate. Ter- and higher polymers may be used if desired. Particularly preferred are the homopolymers and copolymers of acrylic acid. The polyalkenoic acid should be substantially free of unpolymerized monomers.

The amount of polyacid in the dental composition, whether curable or non-curable resin, should be sufficient to provide a desired balance of properties. The polyacid should make up about 10% to 70%, preferably about 30% to 60% by weight, based on the total weight of Part B.

Part B also contains water, which can be present in the product as sold or added by the dental practitioner just prior to use. The water can be distilled, deionized or tap water, with deionized water being preferred. The water represents at least about 1%, preferably about 3% to 35%, more preferably about 5% to 25% of the total dental composition. In general, the amount of water used should be sufficient to provide adequate handling and mixing properties for the dental composition and to permit the transport of ions in the acid-reactive filler-polyacid reaction, particularly the treated FAS glass-polyacid reaction.

Miscellaneous Components

The inventive material may optionally comprise additional adjuvants suitable for use in the oral environment, including colorants, inhibitors, accelerators, flavorants, antimicrobials, fragrance, stabilizers, viscosity modifiers, and fluoride releasing additives. Other suitable adjuvants include agents that impart fluorescence and/or opalescence. Optionally, fumed silica can be used.

The inventive dental composition can further comprise a viscosity modifier such as a hydrogen-bondable compound that is a polymer having a molecular weight greater than about 10,000. Preferably, the polymer has a molecular weight greater than about 20,000, and more preferably greater than about 50,000. Generally, this polymer is present in a small amount of the total composition. Preferably, the polymer present at about 0.05% to 8% more preferably at about 0.1% to 5%, based on the resin component in the inventive composition. The term "resin component" as used in the previous sentence includes curable resins residing in either part A or part B as well as polyacids (curable and non-curable) of Part B. Preferably, the hydrogen-bondable compound contains hydrogen-bond acceptor sites.

Particularly preferred hydrogen-bondable compounds include poly(N-vinylpyrrolidone) polymers (p-NVP). Copolymers of vinylpyrrolidone and other monomers or grafted poly(N-vinylpyrrolidone) with other groups also are preferred, provided that the co-monomers or grafting groups do not contain an adverse amount of active hydrogens for hydrogen bonding. For example, poly(1-vinylpyrrolidone-co-styrene), polyethyloxazoline, poly(1-vinylpyrrolidone-co-vinyl acetate), and so on, are preferred.

The inventive composition can further comprise submicron silica particles to improve the handling properties.

Suitable silica particles include pyrogenic silicas such as AEROSIL series OX 50, 130, 150, and 200, all available from Degussa Corp., and CAB-O-SIL M5 silica available from Cabot Corporation.

EXAMPLES

The following examples are provided to illustrate different embodiments and details of the invention. Although the examples serve this purpose, the particular ingredients and amounts used as well as other conditions and details are not to be construed in a manner that would unduly limit the scope of this invention. Unless otherwise specified, all percentages are in weight percent. Table 1 below is used for convenience and lists the components used in the Examples below.

Abbreviations of Components

| Components | Description |
|---|---|
| A1230 | gamma-(polyalkylene oxide)propyltrimethoxysilane (OSI Specialties, Danbury, CT) |
| A174 | gamma-methacryloxypropyltrimethoxysilane (OSI Specialties, Danbury CT) |
| BHT | 2,6-di-tert-butyl-4-methylphenol |
| CPQ | camphorquinone |
| DPIPF6 | diphenyl iodonium hexafluorophosphate |
| FAS glass | fluoroaluminosilicate glass G018-091(Schott Glass, Westborough, MA) |
| Fujibond LC | GC Fuji Bond LC Standard Set (GC Corp., Tokyo, Japan) |
| HEMA | 2-hydroxyethylmethacrylate |
| oleic acid | 9-octadecenoic acid |
| dimer acid | dimer of 9-octadecenoic acid, EMPOL 1008 (Cognis, Canterbury, CT) |
| MFPA | methacrylated functional polycarboxylic acid, made according to Ex. 11 of U.S. Pat. No. 5,130,347 |
| p-NVP | polyvinyl pyrrolidone (Plasdone K-25; 38,000 $M_n$) (ISP Technologies Inc., Wayne, NJ) |
| S/T FAS | treated FAS glass, treated with silanol or silane |

Diametral Tensile Strength and Compressive Strength Testing

ADA ("American Dental Association") specification No. 9 and ADA specification No. 27 respectively of ISO-test procedure 4049 (1988) were followed for all diametral tensile strength (DTS) and compressive strength (CS) testing. Specifically for CS and DTS, the composition was packed into a 4 mm inside diameter glass tube. The tube was capped with silicone rubber plugs and axially compressed at about 0.28 Mpa, then light cured for 60 seconds by exposure to two oppositely-disposed Visilux 2™ (3M, St. Paul, Minn.) dental curing light units. Each sample was then irradiated for 90 seconds using a Dentacolor XS unit (Kulzer, Inc., Germany). Cured samples were cut on a diamond saw to form cylindrical plugs of 4 mm in diameter an 8 mm long for CS testing and 2 mm long for DTS testing. The samples were stored in distilled water at 37° C. for 24 hours±2 hours. CS and DTS values for each composition were measured using an Instron™ 4505 unit (Instron Corp., Canton, Mass,). The CS testing used a 10 kN load cell and a total of 4 or 5 cylinders were tested The DTS testing was also done with 10 kN load cell and a total of 8 to 10 cylinders were tested.

Adhesive Testing

Adhesive strength to dentin for the Examples below was evaluated by the following procedure. For each example, seven bovine teeth of similar age and appearance were partially embedded in circular acrylic discs. The exposed portion of each tooth was ground flat and parallel to the flat surface of acrylic disc using Grade 120 silicon carbide paper-backed abrasive mounted on a lapidary wheel. This grinding step exposed the dentin. During all grinding and polishing steps, the teeth were continuously rinsed with water. Further grinding and polishing of the teeth was carried out by mounting Grade 600 silicon carbide paper-backed abrasive on the lapidary wheel.

The polished teeth were stored in deionized water and used for testing within 2 hours after polishing. The polished teeth were removed from the water and blotted dry. To produce an even thickness of the Examples for testing, a small square piece of 3M Adhesive tape (Core Series 2-1300, 3M, St. Paul, Minn.), with a hole of 4.76 mm diameter making a "tape hole", was placed on top of the slightly moist dentin. The final dimensions of the tape hole were 0.03 mm in thickness by 4.76 mm in diameter. The adhesive side of the tape hole was placed over the slightly moist dentin. The paste and liquid components (i.e., parts A and B respectively) for each Example and Comparative Example were dispensed from a 3M™ CLICKER™ (3M, St. Paul, Minn.) onto a mixing pad and mixed for 10 to 15 seconds. A brush or ball applicator was used to transfer the formulation into the tape hole. A Visilux 2™ curing light was used to cure the composition for 30 seconds and the tape hole was removed to expose the cured formulation. Adhesion testing molds were made from a 2-mm thick TEFLON™ (E. I. DuPont de Nemours, Wilmington, Del.) sheet. The final dimensions of the mold were 4.76 mm in diameter and 2 mm in thickness. The mold was lined with gelatin and clamped securely on top of the cured formulation in line with the tape hole. A Z-100, A3 shade composite (3M, St. Paul, Minn.) was compressed into the mold and light cured for 40 sec with a Visilux 2™ curing light. The test sample was immediately placed in deionized water and aged for 24 hours at 37° C. The molds were then carefully removed from the teeth, leaving a molded button of the cured inventive formulation attached to each tooth.

The strength of the cured inventive formulation was evaluated by mounting the acrylic disk in a holder clamped in the jaws of an Instron™ 4505 unit with the polished tooth surface oriented parallel to the direction of pull. A loop of orthodontic wire (0.44 mm diameter) was placed around the cured sample adjacent to the polished tooth surface. The ends of the orthodontic wire were clamped in the pulling jaw of the Instron apparatus, thereby placing the bond in shear stress. The bond was stressed until it (or the dentin or the formulation) failed, using a crosshead speed of 2 mm per minute.

Settling Test

A 20 g sample for part A in Table 2 below of each Example and Comparative Example was stored at room temperature (about 25° C.) in a 75 ml plastic jar having a diameter of 3.8 cm. Phase separation, as indicated by the formation of a transparent liquid layer on the top of the sample, was checked daily by visual inspection. After five days, all of the examples were visually inspected and evaluated for the formation of a transparent layer. A dental mixing stick was used to collect the clear liquid, which was then spread over the top of a glass microscope slide. The liquid on glass slide was visually inspected for transparency and the presence of FAS particles.

Working Time Test

The paste (part A in Table 2) and liquid (part B in Table 3) parts of each example were filled into a 3M™ CLICKER™. Two clicks of example material were dispensed onto a mixing pad. Using a stainless steel spatula or dental mixing stick, the two-part formulation was mixed together. Timing began at the start of mixing and ended when the mixed formulation became stringy and tacky between the spatula and mixing pad. The time interval was recorded in seconds.

Silanol Treatment of FAS Glass

A 300 ml beaker with a flat bottom was used as a reaction vessel to prepare the silanol treatment on fluoroalumina silicate reactive glass. The beaker was equipped with a conventional mixing device, such as a magnetic stirrer. A 100 g portion of deionized water was weighed into the beaker and 3.0 g of glacial acetic acid was added to the water. The solution was stirred for 5 to 10 minutes at a speed fast enough to create a small vortex. The pH of the solution was measured at 2.5 to 3.0.

The silanes, A-174 and/or A-1230, were added to the solution in the amounts as indicated in Table 1 for Examples 1 to 6. While adding the indicated amount of silane into the solution, the solution appeared oily and slightly hazy. The silane-water-acid solution was stirred with a small vortex for 1 hour to hydrolyze. After 1 hour, a clear solution was obtained.

A 100 g portion of FAS glass was added into the solution to create a slurry. The glass was added gradually in 5 minutes with stirring. After all the glass was added, the slurry was stirred for an additional 30 minutes. The silanol treated FAS glass slurry was transferred to clean plastic trays for drying. The silanol treated glass was dried for 14 hours at 80° C. in a drying oven. The dried cake was screened through a 74 μm screen to yield silanol treated FAS glass (S/T FAS) for the study.

TABLE 1

Components Used for Silanol Treated FAS Glass

| Example | DI H$_2$O (g) | acetic acid (g) | FAS glass (g) | A 1230 (g) | A 174 (g) |
|---|---|---|---|---|---|
| 1 | 100 | 0.9 | 100 | 2 | 2 |
| 2 | 100 | 0.9 | 100 | 3 | 1 |
| 3 | 100 | 0.9 | 100 | 4 | 0 |
| 4 | 100 | 0.9 | 100 | 2 | 2 |
| 5 | 100 | 0.9 | 100 | 3 | 1 |
| 6 | 100 | 0.9 | 100 | 4 | 0 |

Examples 1 to 6

These examples were made as a two-part formulation. Part A was made by mixing the components listed in Table 2. Any convenient mixing method may be used, but ordinarily the resin components of HEMA, BISGMA and p-NVP, were thoroughly mixed followed by adding the S/T FAS and oleic acid components to the resin mixture. All of the components of Part A were then thoroughly mixed. Part B was made by mixing the components listed in Table 1B. The two-part formulation was loaded into a 3M™ CLICKER™ Dispenser (Minnesota Mining and Manufacturing (3M), St. Paul, Minn.). An equal volume amount of each part was dispensed onto a mixing pad and thoroughly mixed for 10 to 15 seconds to yield the dental composition. Each composition was tested for the various properties listed in Tables 2, 3, and 4.

Comparative Examples A and B

These examples were made according to Examples 1 to 6 except that the FAS glass was not previously treated with silanol.

TABLE 2

Components and Amounts for Part A (g)

| Ex. | HEMA | bis-GMA | p-NVP | S/T FAS | oleic acid | dimer acid |
|---|---|---|---|---|---|---|
| 1 | 19.86 | 6.62 | 0.27 | 73 | 0.25 | 0 |
| 2 | 19.86 | 6.62 | 0.27 | 73 | 0.25 | 0 |
| 3 | 19.86 | 6.62 | 0.27 | 73 | 0.25 | 0 |
| 4 | 19.67 | 6.56 | 0.27 | 73 | 0 | 0.25 |
| 5 | 19.67 | 6.56 | 0.27 | 73 | 0 | 0.25 |
| 6 | 19.67 | 6.56 | 0.27 | 73 | 0 | 0.25 |
| Comp. A | 20.04 | 6.69 | 0.27 | 73* | 0 | 0 |
| Comp. B | 20.04 | 6.59 | 0.27 | 73* | 0 | 0.25 |

*FAS glass without silanol treatment

TABLE 3

Components and Amounts for Part B (g)

| Components | Amount |
|---|---|
| MFPA | 43.00 |
| DI H$_2$O | 16.45 |
| HEMA | 39.25 |
| CPQ | 0.63 |
| DPIPF6 | 0.63 |
| BHT | 0.04 |

TABLE 4

Physical Properties

| Example | Settling for Part A | Working time* | DTS (MPa) | CS (MPa) | Adhesion (MPa) |
|---|---|---|---|---|---|
| 1 | No | 110 | 18.14 | 122.07 | 9.03 |
| 2 | No | 110 | 19.79 | 115.86 | 9.18 |

TABLE 4-continued

| Example | Settling for Part A | Working time* | DTS (MPa) | CS (MPa) | Adhesion (MPa) |
|---|---|---|---|---|---|
| 3 | No | 115 | 14.90 | 109.66 | 11.29 |
| 4 | No | 115 | 18.41 | 120.69 | 10.49 |
| 5 | No | 115 | 20.55 | 106.90 | 10.34 |
| 6 | No | 115 | 14.07 | 98.62 | 9.54 |
| Comp. A | Yes | <15 | n/a | n/a | 7.14 |
| Comp. B | No | <15 | n/a | n/a | 5.61 |
| Fujibond LC | ND** | 90 | 21.03 | 141.38 | 6.76 |

*±10 seconds
**ND not done as formulation is a powder and liquid
n/a is not available as samples were not tested After 5 days of storage, Comp. Example A had formed a separated and transparent liquid layer phase.

As the data in Table 4 indicates, Examples 1 to 6, all of which embody the invention, showed no settling and had adequate working time. They also exhibited acceptable DTS, CS, and adhesion to dentin. Comparative Example A, however, had settling of the filler, and too short of a working time. Its adhesion to dentin was also lower than those of Examples 1 to 6. Although Comparative Example B showed no settling, its working time was short and had lower adhesion to dentin, compared to Examples 1 to 6. The Fujibond LC sample was a powder-liquid system and such disadvantages have been discussed above. It did have adequate DTS and CS, but showed slightly lower adhesion to dentin, as compared to Examples 1 to 6.

All references cited herein, including those cited in the Background section, are incorporated by reference in their entirety.

What is claimed is:

1. A dental composition comprising:
   (a) a part A comprising (i) fluoroaluminosilicate glass that has been surface treated with agents selected from the group consisting of silane, silanol and combinations thereof, and (ii) at least one fatty acid, dimer thereof, or trimer thereof, wherein the fatty acid comprises a $C_4$ to $C_{22}$ alkyl or alkenyl group having a terminal carboxylic acid group; and
   (b) a part B comprising at least one polyacid;
      the composition further comprising at least one resin and at least one initiator, the resin and initiator residing in either part A or part B.

2. The dental composition of claim 1, wherein the polyacid is curable and comprises an ethylenically-unsaturated component.

3. The dental composition of claim 1, wherein the polyacid is a non-curable oligomer or polymer of an unsaturated acid.

4. The dental composition of claim 3, wherein the unsaturated acid is an oxyacid of carbon, sulfur, phosphorous, or boron.

5. The dental composition of claim 4, wherein the oxyacid of carbon is selected from the group consisting of mono-, di-, and tricarboxylic acids.

6. The dental composition of claim 1, wherein the resin is selected from the group consisting of a curable resin and a non-curable resin.

7. The dental composition of claim 6, wherein the curable resin contains at least one ethylenically-unsaturated moiety.

8. The dental composition of claim 6, wherein the non-curable resin is a viscosity modifier that does not contain an acidic group.

9. The dental composition of claim 1, wherein the fatty acid, dimer thereof, or trimer thereof is selected from the group consisting of octadecanoic acid and dimer thereof, 9-octadecenoic acid and dimer thereof, and combinations thereof.

10. The dental composition of claim 1, wherein the silane is selected from the group consisting of gamma-methacryloxypropyltrimethoxysilane, gamma-(polyalkylene oxide) propyltrimethoxysilane, and combinations thereof.

11. The dental composition of claim 1, wherein part B further comprises water.

12. The dental composition of claim 1, wherein
   (a) part A comprises, based on the total weight of the components in part A, (i) from about 10 to 50 parts curable resin, (ii) from about 40 to 80 parts fluoroaluminosilicate glass that has been surface treated with agents selected from the group consisting of silane, silanol, and combinations thereof, and (iii) from about 0.1 to 1 parts fatty acid, dimer thereof, or trimer thereof; and
   (b) part B comprises, based on the total weight of the components of part B, (i) from about 30 to 60 parts polyacid, (ii) from about 25 to 50 parts water, (iii) from about 0.3 to 2 parts of at least one initiator, and (iv) from about 2 to 20 parts curable resin.

13. The dental composition of claim 12, wherein the curable resin of part A comprises 2-hydroxyethyl methacrylate and diglycidyl methacrylate of bis-phenol A, the fatty acid, dimer thereof, or trimer thereof of part A comprises 9-octadecenoic acid or its dimer, the polyacid of part B comprises methacrylated functional polycarboxylic acid, the initiator of part B comprises camphorquinone and diphenyl iodonium hexafluorophosphate, and the curable resin of part B comprises 2-hydroxyethyl methacrylate.

14. The dental composition of claim 13, wherein part A further comprises a viscosity modifier selected from the group consisting of polyvinyl pyrrolidone, poly(1-vinylpyrrolidone-co-styrene), polyethyloxazoline, poly(1-vinylpyrrolidone-co-vinyl acetate), and combinations thereof.

15. The dental composition of claim 14, wherein part A exhibits substantially no settling after 5 days of storage at about 25° C.

16. A kit comprising:
   (a) a dual barrel syringe having a first barrel and a second barrel, the dental composition of claim 1 stored in the barrels such that part A resides in the first barrel and part B resides in the second barrel; and
   (b) instructions to use the syringe.

17. A method of using a dental composition, the method comprising the acts of:
   (a) providing the syringe of dental composition of claim 16;
   (b) dispensing an amount of the dental composition onto a mixing pad;
   (c) mixing parts A and parts B together to form the dental composition; and then
   (d) applying the dental composition to a patient's dental structures.

18. The dental composition of claim 1, wherein the initiator comprises oxidizing agents and reducing agents as part of a thermal redox initiator system.

19. The dental composition of claim 18, wherein at least one of the oxidizing agent and reducing agent are microencapsulated.

* * * * *

UNITED STATES PATENT AND TRADEMARK OFFICE
CERTIFICATE OF CORRECTION

PATENT NO. : 6,613,812 B2
DATED : September 2, 2003
INVENTOR(S) : Bui, Hoa T.

It is certified that error appears in the above-identified patent and that said Letters Patent is hereby corrected as shown below:

Column 1,
Line 18, please delete "Fluoroaluminiosilicate" and insert in place thereof -- Fluoroaluminosilicate --.
Line 34, please delete "metal a" and insert in place thereof -- comprises --.

Column 2,
Line 3, please delete "comprising" and insert in place thereof -- increased --.
Line 31, please delete " increase" and insert in place thereof  -- increased--.

Column 4,
Line 35, please insert -- be -- following "should".
Line 48, please delete "homogenous" and insert in place thereof -- homogeneous --.

Column 5,
Line 64, please delete "ethoxyphenyldimethyl" and insert in place thereof -- ethoxyphenyldimethylmethane --.

Column 11,
Line 54, please delete "an" and insert in place thereof -- and --.

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,613,812 B2
DATED : September 2, 2003
INVENTOR(S) : Bui, Hoa T.

It is certified that error appears in the above-identified patent and that said Letters Patent is hereby corrected as shown below:

Column 1,
Line 18, please delete "Fluoroaluminiosilicate" and insert in place thereof
-- Fluoroaluminosilicate --.
Line 34, please delete "metal a" and insert in place thereof -- a metal --.

Column 2,
Line 3, please delete "comprising" and insert in place thereof -- comprises --.
Line 31, please delete " increase" and insert in place thereof -- increased--.

Column 4,
Line 35, please insert -- be -- following "should".
Line 48, please delete "homogenous" and insert in place thereof -- homogeneous --.

Column 5,
Line 64, please delete "ethoxyphenyldimethyl" and insert in place thereof -- ethoxyphenyldimethylmethane --.

Column 10,
Line 7, please delete "2-choloracrylic" and insert in place thereof -- 2-chloroacrylic --.
Line 7, please delete "3-choloracrylic" and insert in place thereof -- 3-chloroacrylic --.

Column 11,
Line 54, please delete "an" and insert in place thereof -- and --.

This certificate supersedes Certificate of Correction issued August 24, 2004.

Signed and Sealed this

Thirtieth Day of November, 2004

JON W. DUDAS
*Director of the United States Patent and Trademark Office*